US012739963B2

(12) United States Patent
Lu et al.

(10) Patent No.: US 12,739,963 B2
(45) Date of Patent: Sep. 15, 2026

(54) HEAT DISSIPATION STRUCTURE AND NEUTRON BEAM GENERATING DEVICE USING THE SAME

(71) Applicant: HERON NEUTRON MEDICAL CORP., Hsinchu County (TW)

(72) Inventors: Cheng-Ji Lu, Hsinchu County (TW); Zhen-Fan You, Hsinchu County (TW)

(73) Assignee: HERON NEUTRON MEDICAL CORP., Hsinchu County (TW)

( * ) Notice: Subject to any disclaimer, the term of this patent is extended or adjusted under 35 U.S.C. 154(b) by 410 days.

(21) Appl. No.: 18/319,504

(22) Filed: May 18, 2023

(65) Prior Publication Data

US 2024/0349418 A1 Oct. 17, 2024

(30) Foreign Application Priority Data

Apr. 12, 2023 (TW) ................................ 112113705

(51) Int. Cl.

*H05H 3/06* (2006.01)
*A61N 5/10* (2006.01)
*A61N 5/00* (2006.01)

(52) U.S. Cl.

CPC ................ *H05H 3/06* (2013.01); *A61N 5/10* (2013.01); *A61N 2005/007* (2013.01); *A61N 2005/109* (2013.01); *H05H 2242/10* (2013.01)

(58) Field of Classification Search

None
See application file for complete search history.

(56) References Cited

U.S. PATENT DOCUMENTS

2020/0365292 A1* 11/2020 Yeh ........................ F28F 13/12

FOREIGN PATENT DOCUMENTS

| | | | |
|---|---|---|---|
| CN | 107342114 | A | 11/2017 |
| CN | 113347776 | A | 9/2021 |
| CN | 115802577 | A | 3/2023 |
| EP | 3608921 | A1 | 2/2020 |
| EP | 3740046 | A1 | 11/2020 |
| JP | H6-58398 | U | 8/1994 |
| JP | 2004514242 | A | 5/2004 |
| JP | 2011-112413 | A | 6/2011 |

(Continued)

OTHER PUBLICATIONS

Https://web.archive.org/web/20160410145813/https://www.adipools.net/fountains-waterfalls (Year: 2016).*

*Primary Examiner* — James Choi
(74) *Attorney, Agent, or Firm* — CKC & Partners Co., LLC

(57) ABSTRACT

A heat dissipation structure includes a housing. The housing has opposing upper and lower surfaces, and a fluid channel between the upper surface and the lower surface. The fluid channel is configured to allow a fluid to pass through, and the fluid channel includes an inlet buffer tank, an outlet buffer tank and a connecting structure. The inlet buffer tank has opposing first inner wall and second inner wall surfaces. The outlet buffer tank has opposing first inner wall and second inner wall surfaces, and the second inner wall surface is closer to the inlet buffer tank than the first inner wall surface. The connecting structure is disposed on the inlet buffer tank and the outlet buffer tank, in which the connecting structure has a first bevel surface and a second bevel surface connected to the upper surface of the housing.

20 Claims, 6 Drawing Sheets

100

(56) References Cited

FOREIGN PATENT DOCUMENTS

| | | | |
|---|---|---|---|
| JP | 2020-187122 | A | 11/2020 |
| KR | 20110043196 | A | 4/2011 |
| WO | 2017/146205 | A1 | 8/2017 |
| WO | 2022212821 | A1 | 10/2022 |

* cited by examiner

HEAT DISSIPATION STRUCTURE AND NEUTRON BEAM GENERATING DEVICE USING THE SAME

CROSS-REFERENCE TO RELATED APPLICATION

This application claims priority to Taiwan Application Serial Number 112113705, filed Apr. 12, 2023, which is herein incorporated by reference in its entirety.

BACKGROUND

Technical Field

The present disclosure relates to a heat dissipation structure and a neutron beam generating device using the heat dissipation structure.

Description of Related Art

A boron neutron capture therapy (BNCT) is a treatment where boron-containing medicines are combined with tumor cells via blood circulation. A neutron beam is then used to irradiate the location of the tumor tissue as a center. Lithium and helium ions are then produced after boron absorbs the neutrons, which accurately destroy cancer cells without destroying other normal tissues.

For patients, BNCT causes only minimal damage and does not require surgery or anesthesia. Furthermore, in the treatment of brain tumors, if boron neutron capture therapy uses thermal neutrons with lower penetrating ability, the cranium of the patient has to be opened additionally. In contrast, if boron neutron capture therapy uses epithermal neutrons, the cranium of the patient is not required to be opened. The neutron beam can be generated using an accelerator-type neutron source to bombard an ion beam on a target material. However, during the process of generating the neutron beam, the target material may suffer from unexpected damage due to poor heat dissipation.

In this regard, how to effectively solve the heat dissipation problem of the target material during the generation of the neutron beam is one of the targets in the research and development in the related fields.

SUMMARY

One aspect of the present disclosure is a heat dissipation structure.

According to some embodiments of the present disclosure, a heat dissipation structure includes a housing having an upper surface, a lower surface opposite to the upper surface, and a fluid channel located between the upper surface and the lower surface, in which the fluid channel is configured to allow a fluid to pass through. The fluid channel includes an inlet buffer tank, an outlet buffer tank and a connecting structure. The inlet buffer tank has a first inner wall surface and a second inner wall surface opposite the first inner wall surface. The outlet buffer tank has a first inner wall surface and a second inner wall surface opposite the first inner wall surface, and the second inner wall surface of the outlet buffer tank is closer to the inlet buffer tank than the first inner wall surface of the outlet buffer tank, in which the second inner wall surface of the inlet buffer tank is closer to the outlet buffer tank than the first inner wall surface of the inlet buffer tank. The connecting structure located on the inlet buffer tank and the outlet buffer tank, in which the connecting structure has a first bevel surface and a second bevel surface connected to the upper surface of the housing.

In some embodiments, the first bevel surface of the connecting structure and the second bevel surface of the connecting structure taper towards the lower surface of the housing.

In some embodiments, the first bevel surface of the connecting structure is connected to the first inner wall surface of the inlet buffer tank and the second bevel surface of the connecting structure is connected to the first inner wall surface of the outlet buffer tank.

In some embodiments, the first bevel surface of the connecting structure extends downward from the upper surface of the housing, and the first inner wall surface of the inlet buffer tank extends downward from the first bevel surface of the connecting structure.

In some embodiments, the second bevel surface of the connecting structure extends downward from the upper surface of the housing, and the first inner wall surface of the outlet buffer tank extends downward from the second bevel surface of the connecting structure.

In some embodiments, the second inner wall surface of the inlet buffer tank is inclined to the upper surface of the housing, and the second inner wall surface of the outlet buffer tank is inclined to the upper surface of the housing.

In some embodiments, the second inner wall surface of the inlet buffer tank and the second inner wall surface of the outlet buffer tank taper towards the upper surface of the housing.

In some embodiments, a slope of the second inner wall surface of the inlet buffer tank is different from a slope of the second inner wall surface of the outlet buffer tank.

In some embodiments, the slope of the second inner wall surface of the inlet buffer tank is greater than the slope of the second inner wall surface of the outlet buffer tank.

In some embodiments, when the heat dissipation structure is viewed along a direction perpendicular to the upper surface of the housing, the inlet buffer tank has a first arc-shaped profile and the outlet buffer tank has a second arc-shaped profile different from the first arc-shaped profile.

In some embodiments, when the heat dissipation structure is viewed along a direction perpendicular to the upper surface of the housing, an arc length of the second inner wall surface of the inlet buffer tank is greater than an arc length of the second inner wall surface of the outlet buffer tank.

In some embodiments, when the heat dissipation structure is viewed along a direction perpendicular to the upper surface of the housing, a width between the first inner wall surface the second inner wall surface of the inlet buffer tank is different from a width between the first inner wall surface the second inner wall surface of the outlet buffer tank.

In some embodiments, the connecting structure further includes a bottom surface connected to the second inner wall surface of the inlet buffer tank and the second inner wall surface of the outlet buffer tank.

In some embodiments, the bottom surface of the connecting structure is inclined to the second inner wall surface of the inlet buffer tank, and the bottom surface of the connecting structure is inclined to the second inner wall surface of the outlet buffer tank.

In some embodiments, the inlet buffer tank further includes a bottom surface connected to the second inner wall surface of the inlet buffer tank, and the second inner wall surface of the inlet buffer tank is inclined to the bottom surface of the inlet buffer tank.

In some embodiments, the outlet buffer tank further includes a bottom surface connected to the second inner wall surface of the outlet buffer tank, and the second inner wall surface of the outlet buffer tank is inclined to the bottom surface of the outlet buffer tank.

In some embodiments, a distance between the first inner wall surface and the second inner wall surface of the inlet buffer tank along a direction increases from the lower surface of the housing towards the upper surface of the housing.

Another aspect of the present disclosure is a neutron beam generating device.

According to some embodiments of the present disclosure, a neutron beam generating device includes aforementioned heat dissipation structure, an ion beam tubular body and an accelerator. The ion beam tubular body has a channel, in which the ion beam tubular body is located above the heat dissipation structure and directed toward the upper surface of the housing of the heat dissipation structure, and a gap is between the ion beam tubular body and the upper surface of the housing of the heat dissipation structure. The accelerator is connected to the ion beam tubular body and is configured to emit an ion beam toward the upper surface of the housing of the heat dissipation structure through the channel.

In some embodiments, the ion beam tubular body is perpendicular to the upper surface of the housing of the heat dissipation structure.

In some embodiments, two sides of the channel of the ion beam tubular body are respectively aligned with the first bevel surface and the second bevel surface of the connecting structure.

In the aforementioned embodiments, since the connecting structure has the first bevel surface and the second bevel surface connecting the upper surface of the housing, the fluid in the fluid channel can be concentrated at a center of the housing (i.e., a center the target corresponding to the center of the housing) and has a faster flowing speed, thereby enhancing the effect of removing the heat from the target. Furthermore, through this mechanism, the heat dissipation structure is suitable (or adaptable) to be applied in the neutron beam generating device.

It is to be understood that both the foregoing general description and the following detailed description are by examples, and are intended to provide further explanation of the disclosure as claimed.

BRIEF DESCRIPTION OF THE DRAWINGS

The disclosure can be more fully understood by reading the following detailed description of the embodiment, with reference made to the accompanying drawings as follows.

DETAILED DESCRIPTION

Figure 1:
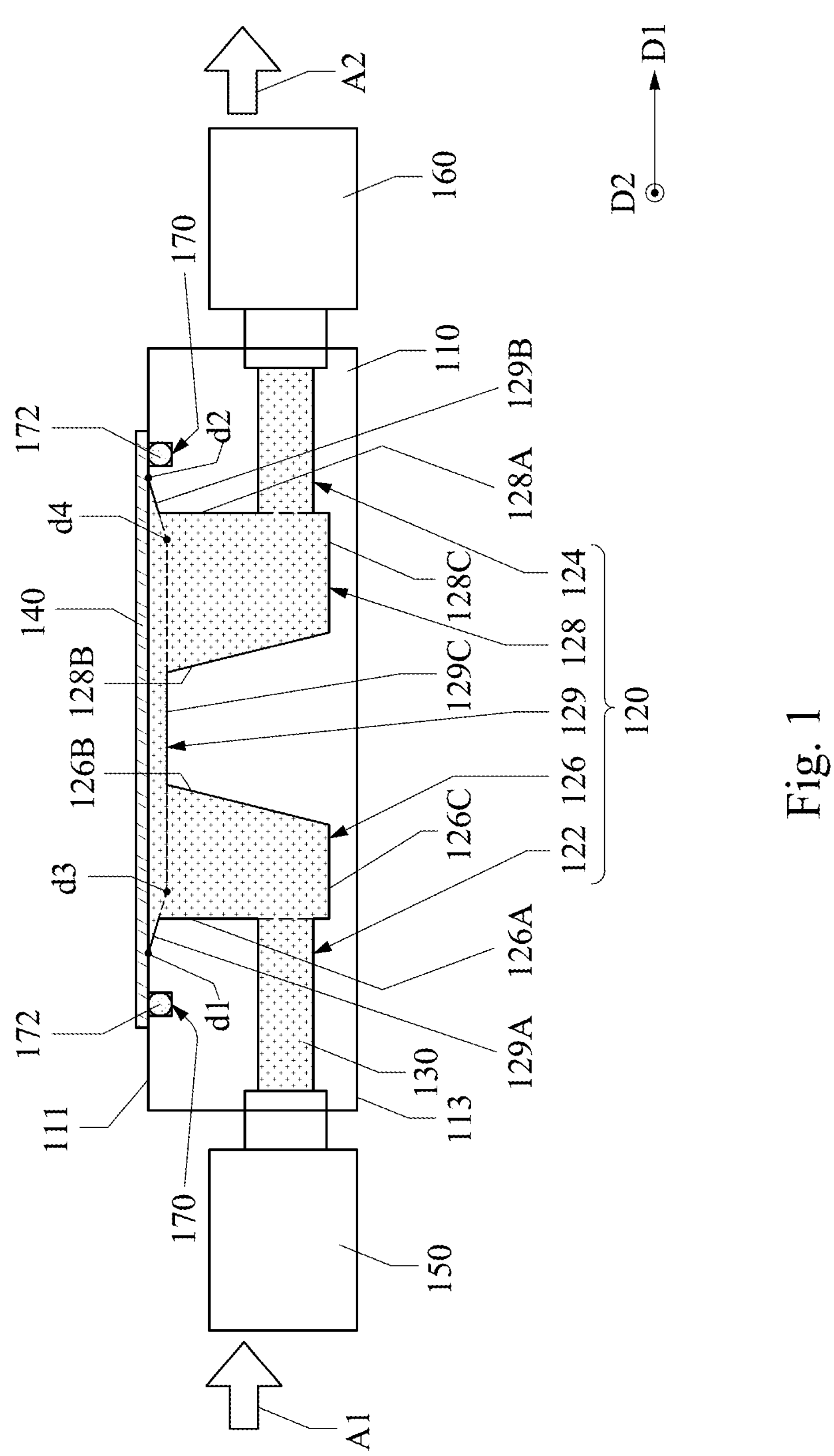
FIG. 1 is a cross-section view of a heat dissipation structure in accordance with an embodiment of the present disclosure.

Reference will now be made in detail to the present embodiments of the disclosure, examples of which are illustrated in the accompanying drawings. Wherever possible, the same reference numbers are used in the drawings and the description to refer to the same or like parts.

As used herein, "around," "about," "approximately," or "substantially" shall generally mean within 20 percent, or within 10 percent, or within 5 percent of a given value or range. Numerical quantities given herein are approximate, meaning that the term "around," "about," "approximately," or "substantially" can be inferred if not expressly stated.

Figure 2:
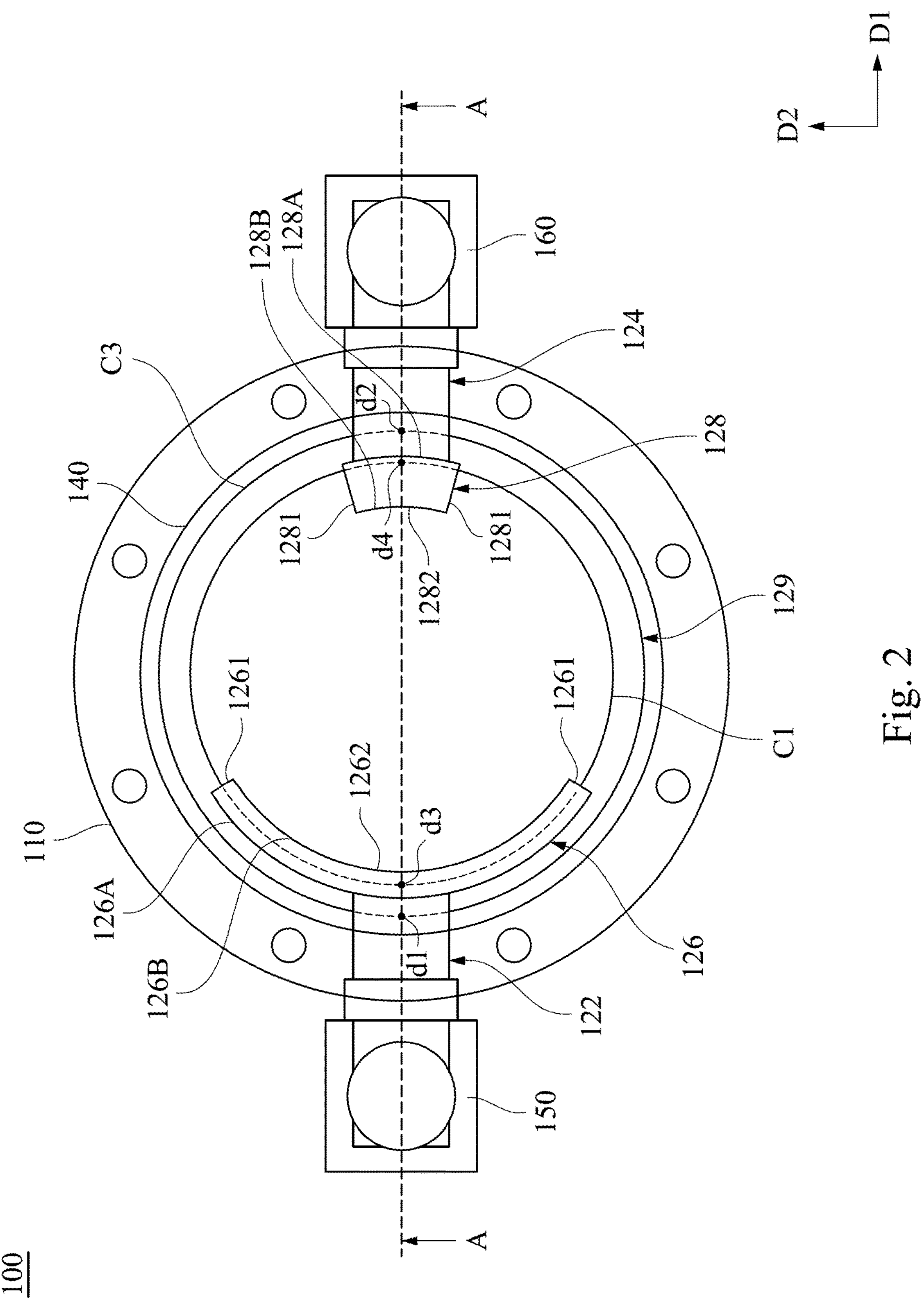
FIG. 2 is a top view of FIG. 1.

FIG. 1 is a cross-section view of a heat dissipation structure 100 in accordance with an embodiment of the present disclosure, and FIG. 2 is a top view of FIG. 1. FIG. 1 illustrates a cross-sectional view taken along line A-A of FIG. 2, and FIG. 2 is a cross-sectional projection when the heat dissipation structure 100 is viewed along a direction perpendicular to the upper surface 111 of the housing 110. For convenience of illustration, FIG. 1 and FIG. 2 show a first direction D1 and a second direction D2, in which the first direction D1 is different from the second direction D2. For example, the first direction D1 is the lateral direction of FIG. 2, and the second direction D2 is the longitudinal direction of FIG. 2, in which the first direction D1 is perpendicular to the second direction D2.

The heat dissipation structure 100 includes a housing 110. The housing 110 has an upper surface 111 and a lower surface 113 opposite to the upper surface 111, and a fluid channel 120 located between the upper surface 111 and the lower surface 113, in which the fluid channel 120 is configured to allow a fluid 130 to pass through. The fluid channel 120 includes an inlet buffer tank 126, an outlet buffer tank 128, and a connecting structure 129. The inlet buffer tank 126 has a first inner wall surface 126A and a second inner wall surface 126B opposite to the first inner wall surface 126A, in which the second inner wall surface 126B of the inlet buffer tank 126 is closer to the outlet buffer tank 128 than the first inner wall surface 126A of the inlet buffer tank 126. The outlet buffer tank 128 has a first inner wall surface 128A and a second inner wall surface 128B opposite to the first inner wall surface 128A, in which the second inner wall surface 128B of the outlet buffer tank 128 is closer to the inlet buffer tank 126 than the first inner wall surface 128A of the outlet buffer tank 128. The connecting structure 129 is located on the inlet buffer tank 126 and the outlet buffer tank 128, in which the connecting structure 129 has a first bevel surface 129A and a second bevel surface 129B connected to the upper surface 111 of the housing 110. With the above configuration, the fluid 130 in the fluid channel 120 can be concentrated at (or directed into) a center of the housing 110 (i.e., a center of the target 140 corresponding to the center of the housing 110) and has a faster flowing speed, thereby improving the effect of removing heat from the target 140.

The connecting structure 129 may be referred as an accommodating space for the fluid channel 120 at the upper surface 111 of the housing 110. In other words, the connecting structure 129 is located between the target 140 and the buffer tanks (inlet buffer tank 126 and outlet buffer tank 128). The fluid 130 flows from the inlet buffer tank 126 into the connecting structure 129, and then flows from the connecting structure 129 to the outlet buffer tank 128. The first bevel surface 129A of the connecting structure 129 is connected to the upper surface 111 of the housing 110 and the first inner wall surface 126A of the inlet buffer tank 126. In greater details, the first bevel surface 129A of the connecting structure 129 is inclined to the upper surface 111 of the housing 110 and extends downward from the upper surface 111 of the housing 110. The first inner wall surface 126A of the inlet buffer tank 126 extends downward from the first bevel surface 129A of the connecting structure 129. In some embodiments, in FIG. 1, the first inner wall surface 126A of the inlet buffer tank 126 is perpendicular to the upper surface 111 and/or lower surface 113 of the housing 110. The second bevel surface 129B of the connecting structure 129 is connected to the upper surface 111 of the housing 110 and the first inner wall surface 128A of the outlet buffer tank 128. In greater details, the second bevel surface 129B of the connecting structure 129 is inclined to the upper surface 111 of the housing 110 and extends downward from the upper surface 111 of the housing 110. The first inner wall surface 128A of the outlet buffer tank 128 extends downward from the second bevel surface 129B of the connecting structure 129. In some embodiments, in FIG. 1, the first inner wall surface 128A of the outlet buffer tank 128 is perpendicular to the upper surface 111 and/or the lower surface 113 of the housing 110.

In some embodiments, the first bevel surface 129A and the second bevel surface 129B of the connecting structure 129 are symmetrically arranged. For example, an inner angle between the upper surface 111 and the first bevel surface 129A is substantially equal to an angle between the upper surface 111 and the second bevel surface 129B (or a slope of the first bevel surface 129A is substantially equal to a slope of the second bevel surface 129B), but the present disclosure is not limited thereto. In some embodiments, the first bevel surface 129A of the connecting structure 129 and the second bevel surface 129B of the connecting structure 129 gradually taper from the upper surface 111 of the housing 110 towards the lower surface 113 of the housing 110. For example, a first inner angle between the first bevel surface 129A of the connecting structure 129 and the first inner wall surface 126A of the inlet buffer tank 126 is greater than 180 degrees, and a second inner angle between the second bevel surface 129B of the connecting structure 129 and the first inner wall surface 128A of the outlet buffer tank 128 is greater than 180 degrees. In some embodiments, the first inner angle is substantially equal to the second inner angle, but the present disclosure is not limited thereto.

In some embodiments, the connecting structure 129 has a bottom surface 129C that is connected to the second inner wall surface 126B of the inlet buffer tank 126 and the second inner wall surface 128B of the outlet buffer tank 128, in which the bottom surface 129C of the connecting structure 129 is inclined to the second inner wall surface 126B of the inlet buffer tank 126 and/or the second inner wall surface 128B of the outlet buffer tank 128. In some embodiments, the connecting structure 129 is located between the upper surface 111 of the housing 110 and the buffer tanks (inlet buffer tank 126 and outlet buffer tank 128), and the fluid 130 can physically contact the target 140 through the connecting structure 129, thereby achieving the effect of cooling the target 140. In other words, the connecting structure 129 includes a first portion located directly above the inlet buffer tank 126, a second portion located directly above the outlet buffer tank 128, and a third portion connected to the first portion and the second portion (i.e., the third portion is located directly above the bottom surface 129C). In some embodiments, as shown in FIG. 1 and FIG. 2, the fluid 130 in the fluid channel 120 is constrained by the first bevel surface 129A and the second bevel surface 129B of the connecting structure 129, such that the fluid 130 is concentrated towards/at the center of the housing 110 (e.g., the fluid 130 is restricted in a region directly above the bottom surface 129C), thereby improving the effect of removing heat from the target 140. For example, the first bevel surface 129A has a point d1 on the upper surface 111 of the housing 110, and the second bevel surface 129B has a point d2 on the upper surface 111 of the housing 110. The point d1 and the point d2 in FIG. 1 may define a circle C3 in FIG. 2. For example, the connecting structure 129 is referred as a disc-shaped structure located above the inlet buffer tank 126 and the outlet buffer tank 128. When the heat dissipation structure 100 is viewed along the direction perpendicular to the upper surface 111 of the housing 110, a cross-sectional projection of the fluid channel 120 between points d1 and d2 (i.e., a cross-sectional projection of the connecting structure 129) along the first direction D1 has a disc (or circular) profile and the aforementioned cross-sectional projection is shown as the circle C3 in FIG. 2. For example, when the heat dissipation structure 100 is viewed along the direction perpendicular to the upper surface 111 of the housing 110, the first bevel surface 129A of the connecting structure 129, the bottom surface 129C and its extension surface (i.e., a surface of the bottom surface 129C extends into the inlet buffer tank 126 and the outlet buffer tank 128) of the connecting structure 129, and the second bevel surface 129B of the connecting structure 129 collectively form a disk-shaped profile, in which an edge of the disk-shaped profile is shown as the circle C3 in FIG. 2. The point d1 and the point d2 may be respectively referred as endpoints (or edges) of the circle C3 on the first bevel surface 129A and the second bevel surface 129B. Alternatively, the point d1 and the point d2 may be respectively referred as intersections of the circle C3 with line A-A in FIG. 2. The first bevel surface 129A and the second bevel surface 129B can limit the fluid 130 from flowing out of the range of the circle C3. In some embodiments, the slope of the first bevel surface 129A and the slope of the second bevel surface 129B vary depending on a pressure of the fluid 130. Specifically, the bottom surface 129C (or its extension surface) of the connecting structure 129 intersects with an extension surface of the first bevel surface 129A at a (hypothetical) point d3. The position of point d3 between the first inner wall surface 126A of the inlet buffer tank 126 and the bottom surface 129C (or its extension surface) of the connecting structure 129 can be adjusted based on the pressure of the fluid 130, thereby determining the slope of the first bevel surface 129A. For example, the point d3 is located within the inlet buffer tank 126 (i.e., directly above the bottom surface 126C of the inlet buffer tank 126) or on the bottom surface 129C of the connecting structure 129. Similarly, the bottom surface 129C of the connecting structure 129 (or its extension surface) intersects with an extension surface of the second bevel surface 129B at a (hypothetical) point d4. The position of point d4 between the first inner wall surface 128A of the outlet buffer tank 128 and the bottom surface 129C (or its extension surface) of the connecting structure 129 can be adjusted based on the pressure of the fluid 130, thereby determining the slope of the second bevel surface 129B. For example, the point d4 is located within the outlet buffer tank 128 (i.e., directly above the bottom surface 128C of the outlet buffer tank 128) or on the bottom surface 129C of the connecting structure 129. The point d3 and the point d4 in FIG. 1 can define a circle C1 in FIG. 2. In greater details, when the heat dissipation structure 100 is viewed along the direction perpendicular to the upper surface 111 of the housing 110, a cross-section projection of the fluid channel 120 between the point d3 and the point d4 (i.e., a portion of the inlet buffer tank 126, a portion of the outlet buffer tank 128, and a portion of the connecting structure 129) along the first direction D1 has a disk (or circular) profile, and is shown as the circle C1 in FIG. 2. The point d3 and the point d4 may be respectively referred as intersections of the circle C1 with line A-A in FIG. 2.

In some embodiments, the target 140 is located above the connecting structure 129 such that the fluid 130 is physically in contact with the target 140 through the connecting structure 129 to achieve the effect of cooling the target 140. In some embodiments, the target 140 fully covers the connecting structure 129. In some embodiments, since the first bevel surface 129A of the connecting structure 129 can limit the fluid 130 to concentrate at the center of the target 140, the effect of cooling target 140 and the effect of enhancing the heat dissipation of the target 140 can be achieved.

In some embodiments, in FIG. 1 (i.e., the cross-sectional view taken along line A-A in FIG. 2), the first inner wall surface 126A of the inlet buffer tank 126 is parallel to the first inner wall surface 128A of the outlet buffer tank 128. Alternatively, in FIG. 2, the first inner wall surface 126A of the inlet buffer tank 126 and the first inner wall surface 128A of the outlet buffer tank 128 can form circular arc of concentric circles.

In some embodiments, as shown in FIG. 1, the second inner wall surface 126B of the inlet buffer tank 126 is inclined to the upper surface 111 and/or lower surface 113 of the housing 110. In greater details, as shown in FIG. 1, the inlet buffer tank 126 further includes a bottom surface 126C connected to the second inner wall surface 126B, and the second inner wall surface 126B of the inlet buffer tank 126 is inclined to the bottom surface 126C. As a result, the pressure of the fluid 130 can be reduced and the heat dissipation efficiency can be increased. In some embodiments, as shown in FIG. 1, the second inner wall surface 128B of the outlet buffer tank 128 is inclined to the upper surface 111 and/or lower surface 113 of the housing 110. In greater details, as shown in FIG. 1, the outlet buffer tank 128 further includes a bottom surface 128C connected to the second inner wall surface 128B, and the second inner wall surface 128B of the outlet buffer tank 128 is inclined to the bottom surface 128C. As a result, the pressure of the fluid 130 can be reduced and turbulence or negative pressure can be avoided. In some embodiments, in FIG. 1 (i.e., the cross-sectional view taken along line A-A in FIG. 2), the second inner wall surface 126B of the inlet buffer tank 126 is not parallel to the first inner wall surface 126A of the inlet buffer tank 126, and the second inner wall surface 128B of the outlet buffer tank 128 is not parallel to the first inner wall surface 128A of the outlet buffer tank 128. In some embodiments, as shown in FIG. 1, the bottom surface 126C of the inlet buffer tank 126 is aligned with the bottom surface 128C of the outlet buffer tank 128. For example, in FIG. 1, the bottom surface 126C of the inlet buffer tank 126 and the bottom surface 128C of the outlet buffer tank 128 are substantially at the same horizontal level. In some embodiments, as shown in FIG. 1, the bottom surface 129C of the connecting structure 129 is above the bottom surface 126C of the inlet buffer tank 126, and the bottom surface 129C of the connecting structure 129 is above the bottom surface 128C of the outlet buffer tank 128. In some embodiments, as shown in FIG. 1, a vertical projection of the bottom surface 129C of the connecting structure 129 on the upper surface 111 of the housing 110 is not overlapped with a vertical projection of the bottom surface 126C of the inlet buffer tank 126 (or the bottom surface 128C of the outlet buffer tank 128) on the upper surface 111 of the housing 110.

In some embodiments, the second inner wall surface 126B of the inlet buffer tank 126 and the second inner wall surface 128B of the outlet buffer tank 128 gradually taper towards the upper surface 111 of the housing 110. As a result, the fluid 130 in the fluid channel 120 can be concentrated at the center of the housing 110, thereby increasing the heat dissipation efficiency. In some embodiments, a distance between the first inner wall surface 126A and the second inner wall surface 126B of the inlet buffer tank 126 along the first direction D1 increases from the lower surface 113 of the housing 110 towards the upper surface 111 of the housing 110. Similarly, a distance between the first inner wall surface 128A and the second inner wall surface 128B of the outlet buffer tank 128 along the first direction D1 increases from the lower surface 113 of the housing 110 towards the upper surface 111 of the housing 110. In some embodiments, an inner angle between the second inner wall surface 126B of the inlet buffer tank 126 and the bottom surface 126C of the inlet buffer tank 126 is greater than 90 degrees, and an inner angle between the second inner wall surface 128B of the outlet buffer tank 128 and the bottom surface 128C of the outlet buffer tank 128 is greater than 90 degrees. In some embodiments, a slope of the second inner wall surface 126B of the inlet buffer tank 126 (e.g., the inner angle between the second inner wall surface 126B and the bottom surface 126C) is different from a slope of the second inner wall surface 128B of the outlet buffer tank 128 (e.g., the inner angle between the second inner wall surface 128B and the bottom surface 128C). For example, the slope of the second inner wall surface 126B of the inlet buffer tank 126 is greater than the slope of the second inner wall surface 128B of the outlet buffer tank 128.

In some embodiments, a material of the housing 110 is a metal, such as aluminum. The housing 110 can be integrally formed and can also be formed from assembly. The upper surface 111 of the housing 110 may be referred as the topmost surface of the housing 110, and the lower surface 113 of the housing 110 may be referred as the bottommost surface of the housing 110. The housing 110 may be configured to carry a target 140, in which the target 140 is a plate-shaped target. The target 140 is located on the upper surface 111 of the housing 110 and covers an entirety of the connecting structure 129. Specifically, the target 140 fully covers the first bevel surface 129A of the connecting structure 129, the bottom surface 129C of the connecting structure 129, and the second bevel surface 129B of the connecting structure 129.

The fluid channel 120 further includes an inlet channel 122 and an outlet channel 124. The inlet channel 122 and the outlet channel 124 are located at opposite ends of the housing 110. The inlet channel 122 and the outlet channel 124 of the fluid channel 120 may extend in the same direction (e.g., the first direction D1). The first inner wall surface 126A of the inlet buffer tank 126 is connected to the inlet channel 122, and the second inner wall surface 126B of the inlet buffer tank 126 is closer to the outlet channel 124 than the first inner wall surface 126A of the inlet buffer tank 126. The first inner wall surface 128A of the outlet buffer tank 128 is connected to the outlet channel 124, and the second inner wall surface 128B of the outlet buffer tank 128 is closer to the inlet channel 122 than the first inner wall surface 128A of the outlet buffer tank 128.

In some embodiments, the heat dissipation structure 100 further includes an inlet pipe 150 and an outlet pipe 160 connected to opposite ends of the housing 110. The inlet pipe 150 is connected to the inlet channel 122 of the housing 110, and the outlet pipe 160 is connected to the outlet channel 124 of the housing 110. In some embodiments, the heat dissipation structure 100 further includes a pressurization device (not shown) configured to deliver the fluid 130 from the inlet pipe 150 into the inlet channel 122 of the housing 110, as indicated by arrow A1, such that the fluid 130 may flow through the inlet buffer tank 126 and the connecting structure 129 and in contact with the target 140. Subsequently, the fluid 130 may exit from the housing and enter into the outlet pipe 160 through the outlet buffer tank 128 and the outlet channel 124, as indicated by arrow A2.

Figure 3:
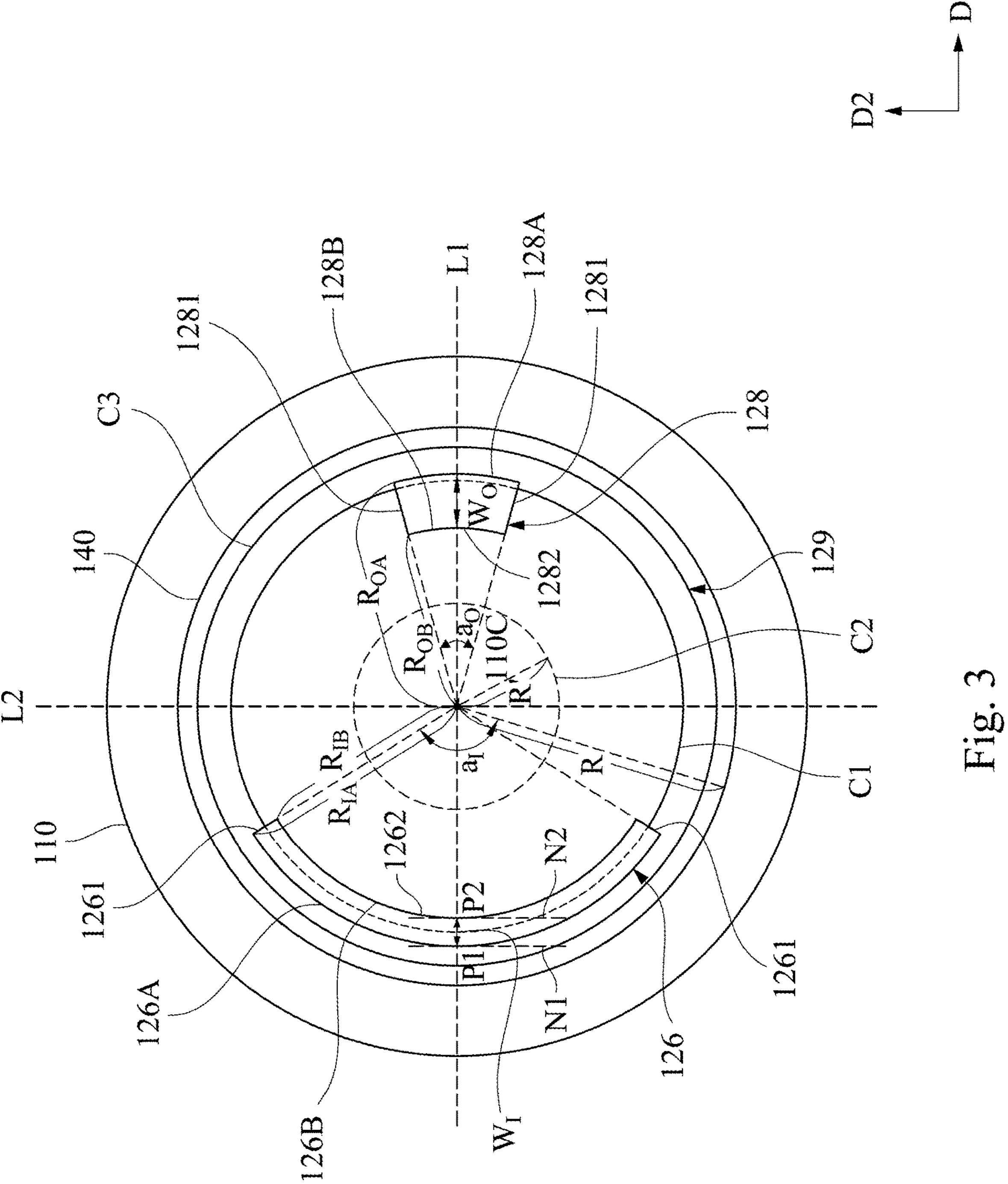
FIG. 3 shows a partially enlarged view of FIG. 2.

FIG. 3 shows a partially enlarged view of FIG. 2. For convenience of explanation, the inlet pipe 150, the inlet channel 122, the outlet channel 124, and the outlet pipe 160 are shown in FIG. 2 and are omitted in FIG. 3. As shown in FIG. 3, the housing 110, the target 140, the circle C1, the circle C3, a circle with the first inner wall surface 126A of the inlet buffer tank 126 as a circumference, and a circle with the first inner wall surface 128A of the outlet buffer tank 128 as a circumference are concentric. In some embodiments, the housing 110 and the target 140 have a disc-shaped profile, and the housing 110 and the target 140 share a center 110C. That is, the center 110C of the housing 110 is the same as the center 110C of the target 140. The first line L1 is a hypothetical line that passes through the center 110C and extends along the first direction D1, and the second line L2 is a hypothetical line that passes through the center 110C and extends along the second direction D2, in which the first line L1 is perpendicular to the second line L2.

Referring to FIG. 1 to FIG. 3, when the heat dissipation structure 100 is viewed along the direction perpendicular to the upper surface 111 of the housing 110 (i.e., the top view of the heat dissipation structure 100 shown in FIG. 2 and FIG. 3), the inlet buffer tank 126 has a first arc-shaped profile (e.g., circular arc profile), and the outlet buffer tank 128 has a second arc-shaped profile (e.g., circular arc profile) different from the first arc-shaped profile. As a result, the fluid 130 in the fluid channel 120 can be concentrated at (or towards) the center of the housing 110 (i.e., the center of the target 140 corresponding to the center of the housing 110) with a faster flowing speed, thereby enhancing the effect of removing heat from the target 140. In some embodiments, an arc length of the first inner wall surface 126A of the inlet buffer tank 126 is greater than an arc length of the first inner wall surface 128A of the outlet buffer tank 128. An arc length of the second inner wall surface 126B of the inlet buffer tank 126 is greater than an arc length of the second inner wall surface 128B of the outlet buffer tank 128. In other words, the inlet buffer tank 126 corresponding to the center 110C forms a central angle $a_I$, and the outlet buffer tank 128 corresponding to the center 110C forms a central angle $a_O$, in which the central angle $a_I$ of the inlet buffer tank 126 is greater than the central angle $a_O$ of the outlet buffer tank 128. As a result, when the fluid 130 flows from the inlet buffer tank 126 to the outlet buffer tank 128 through the connecting structure 129, the fluid 130 may be concentrated at the center of the housing 110 (e.g., within the range of the circle C2) and produce a flowing speed variation. Specifically, the fluid 130 has a faster flowing speed at the center of the housing 110 (e.g., within the range of the circle C2), thereby enhancing the effect of removing heat from the target 140. In some embodiments, the central angles $a_I$ of the inlet buffer tank 126 and the central angles $a_O$ of the outlet buffer tank 128 can be respectively adjusted depending on a half-width of the incident ion beam (e.g., ion beam 230 in FIG. 5). For example, the central angles $a_I$ of the inlet buffer tank 126 and the central angles $a_O$ of the outlet buffer tank 128 are respectively in a range of about 40 degrees to about 120 degrees.

In some embodiments, as shown in FIG. 3, a width $W_I$ between the first inner wall surface 126A and the second inner wall surface 126B of the inlet buffer tank 126 along the first line L1 is different from a width $W_O$ between the first inner wall surface 128A and the second inner wall surface 128B of the outlet buffer tank 128 along the first line L1. Furthermore, the width $W_I$ between the first inner wall surface 126A and the second inner wall surface 126B of the inlet buffer tank 126 along the first line L1 is smaller than the width $W_O$ between the first inner wall surface 128A and the second inner wall surface 128B of the outlet buffer tank 128 along the first line L1. The width $W_I$ of the inlet buffer tank 126 and the width $W_O$ of the outlet buffer tank 128 may be adjusted based on the pressure of the fluid 130 in the inlet pipe 150. It is noted that the term of "width" herein means a vertical distance between the two inner wall surfaces (e.g., the first inner wall surface 126A and the second inner wall surface 126B) of the inlet buffer tank 126 or a vertical distance between the two inner wall surfaces (e.g., the first inner wall surface 128A and the second inner wall surface 128B) of the outlet buffer tank 128. For example, in the case of the inlet buffer tank 126, the first inner wall surface 126A has a point P1 thereon, and the second inner wall surface 126B has a point P2 closest to the point P1 thereon. A distance between a normal line N1 perpendicular to the point P1 and a normal line N2 perpendicular to the point P2 is defined as the width $W_I$ (i.e. vertical distance) between the first inner wall surface 126A and the second inner wall surface 126B.

In some embodiments, a minimum distance $R_{IA}$ (or a radius of the circle with the first inner wall surface 126A of the inlet buffer tank 126 as the circumference) between the first inner wall surface 126A of the inlet buffer tank 126 and the center 110C of the housing 110 is different from a minimum distance $R_{OA}$ (or a radius of the circle with the first inner wall surface 128A of the outlet buffer tank 128 as the circumference) between the first inner wall surface 128A of the outlet buffer tank 128 and the center 110C of the housing 110. For example, the minimum distance $R_{IA}$ between the first inner wall surface 126A of the inlet buffer tank 126 and the center 110C of the housing 110 is greater than the minimum distance $R_{OA}$ between the first inner wall surface 128A of the outlet buffer tank 128 and the center 110C of the housing 110. Alternatively, the minimum distance $R_{IA}$ between the first inner wall surface 126A of the inlet buffer tank 126 and the center 110C of the housing 110 is smaller than or equal to the minimum distance $R_{OA}$ between the first inner wall surface 128A of the outlet buffer tank 128 and the center 110C of the housing 110, but the present disclosure is not limited thereto. In addition, a minimum distance $R_{IB}$ (or a radius of the circle with the second inner wall surface 126B of the inlet buffer tank 126 as the circumference) between the second inner wall surface 126B of the inlet buffer tank 126 and the center 110C of the housing 110 is different from a minimum distance $R_{OB}$ (or a radius of the circle with the second inner wall surface 128B of the outlet buffer tank 128 as the circumference) between the second inner wall surface 128B of the outlet buffer tank 128 and the center 110C of the housing 110. For example, the minimum distance $R_{IB}$ between the second inner wall surface 126B of the inlet buffer tank 126 and the center 110C of the housing 110 is greater than the minimum distance $R_{OB}$ between the second inner wall surface 128B of the outlet buffer tank 128 and the center 110C of the housing 110. Alternatively, in some embodiments, the minimum distance $R_{IB}$ between the second inner wall surface 126B of the inlet buffer tank 126 and the center 110C of the housing 110 is smaller than or equal to the minimum distance $R_{OB}$ between the second inner wall surface 128B of the outlet buffer tank 128 and the center 110C of the housing 110, but the present disclosure is not limited thereto. In some embodiments, the inlet buffer tank 126 has two end portions 1261 and a central portion 1262 between the two end portions 1261, in which the central portion 1262 of the inlet buffer tank 126 is connected to the inlet channel 122 and the central portion 1262 is closer to the inlet channel 122 than the two end portions 1261. Similarly, the outlet buffer tank 128 has two end portions 1281 and a central portion 1282 between the two end portions 1281, in which the central portion 1282 of the outlet buffer tank 128 is connected to the outlet channel 124 and the central portion 1282 is closer to the outlet channel 124 than the two end portions 1281. The minimum distance $R_{IB}$ between one of the two end portions 1261 of the inlet buffer tank 126 and the center 110C of the housing 110 is greater than the minimum distance $R_{OB}$ between one of the two end portions 1281 of the outlet buffer tank 128 and the center 110C of the housing 110. In some embodiments, the minimum distance $R_{IA}$ between the first inner wall surface 126A of the inlet buffer tank 126 and the center 110C of the housing 110 and the minimum distance $R_{OA}$ between the first inner wall surface 128A of the outlet buffer tank 128 and the center 110C of the housing 110 can be adjusted based on the half-width of the incident ion beam (e.g., the ion beam 230 in FIG. 5). In addition, the minimum distance $R_{IB}$ between the second inner wall surface 126B of the inlet buffer tank 126 and the center 110C of the housing 110 and the minimum distance $R_{OB}$ between the second inner wall surface 128B of the outlet buffer tank 128 and the center 110C of the housing 110 can be adjusted based on the half-width of the incident ion beam (e.g., the ion beam 230 in FIG. 5).

In some embodiments, with the configuration of the inlet buffer tank 126, the outlet buffer tank 128 and the connecting structure 129 of the present disclosure, the fluid 130 in the fluid channel 120 can have the faster flowing speed at the center of the housing 110 (e.g., within the range of the circle C2), and the fluid 130 can provide better heat dissipation effect (cooling effect) to the target 140. It also means that the heat dissipation effect (cooling effect) provided by the fluid 130 to the target 140 is decreased gradually from the center of the housing 110 (e.g., within the range of the circle C2) to the two sides of the housing 110 along the second direction D2. With this mechanism, the heat dissipation structure 100 is suitable (or adaptable) to carry out heat dissipation to the target 140 with heat distribution in the pattern of "gradual decrease to the two sides from the center", in which "gradual decrease to the two sides from the center" can be, for example, of Gaussian distribution, normal distribution or bell-shaped distribution.

In some embodiments, as shown in FIG. 1, the heat dissipation structure 100 further includes sealing gaskets 172. The housing 110 may have grooves 170 on the upper surface 111, and the sealing gaskets 172 can be placed within the grooves 170. The sealing gaskets 172 can provide air tightness and water-proof effect. It is noted that the grooves 170 and sealing gaskets 172 are illustrated in FIG. 1 and are not illustrated (i.e., omitted) in FIGS. 2 and 3 for the sake of simplicity.

As mentioned above, since the heat dissipation structure 100 is configured to carry out heat dissipation to the target 140 with heat distribution in the pattern of gradual decrease to the two sides from the center, the heat dissipation structure 100 is configured to be applied to device which would cause the target 140 to have this pattern of heat distribution during operation, such as a neutron beam generating device.

Figure 4:
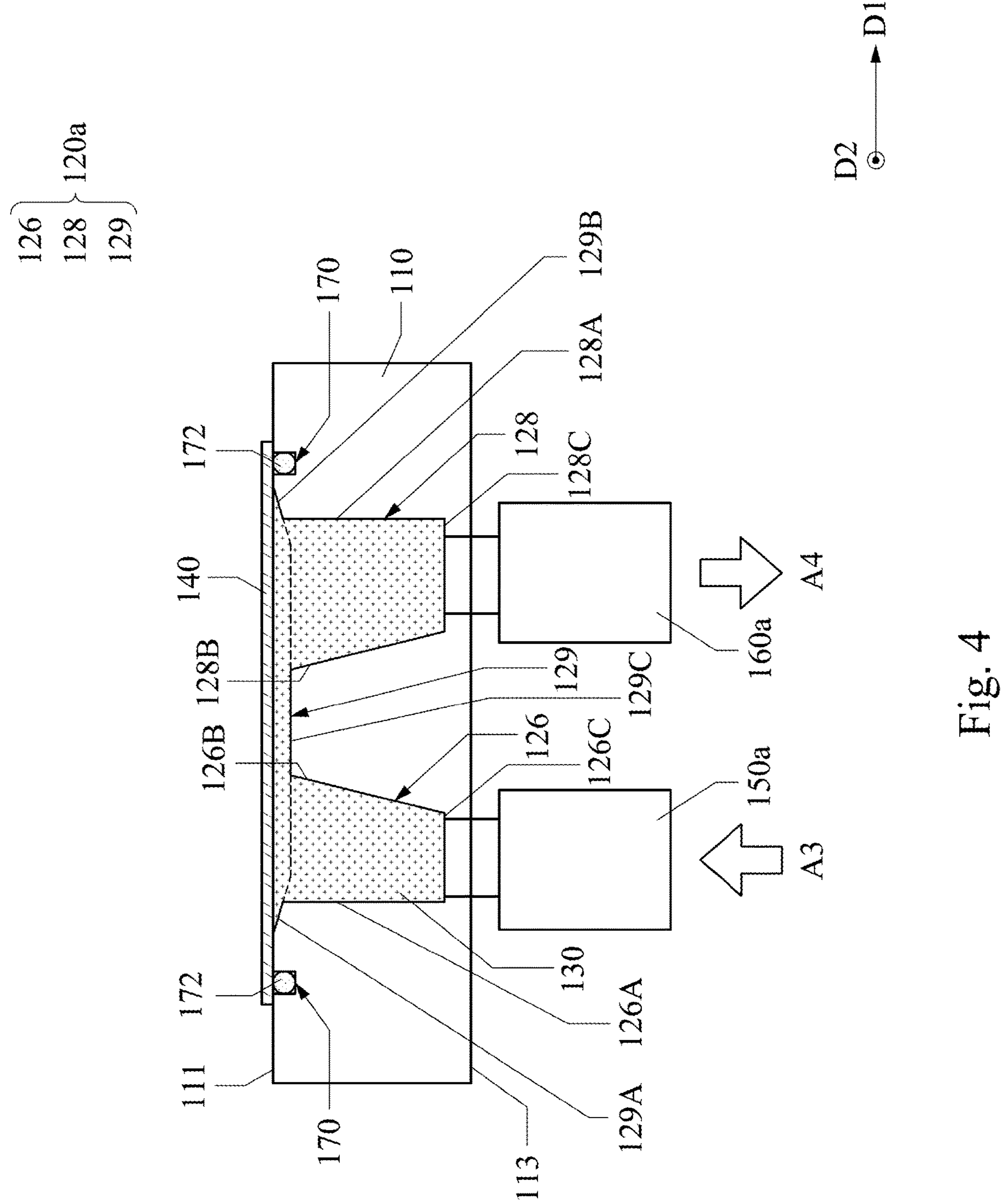
FIG. 4 is a cross-section view of a heat dissipation structure in accordance with another embodiment of the present disclosure.

FIG. 4 is a schematic view of a heat dissipation structure 100*a* in accordance with another embodiment of the present disclosure. The heat dissipation structure 100*a* of FIG. 4 is substantially the same as the heat dissipation structure 100 of FIG. 1, and the difference is the configuration of an inlet pipe 150*a* and an outlet pipe 160*a* of the heat dissipation structure 100*a*. The inlet pipe 150*a* and the outlet pipe 160*a* of the heat dissipation structure 100*a* are located on the lower surface 113 of the housing 110. The inlet pipe 150*a* is connected to the inlet buffer tank 126 of the fluid channel 120*a*, and the outlet pipe 160*a* is connected to the outlet buffer tank 128 of the fluid channel 120*a*. In some embodiments, the heat dissipation structure 100 may further include a pressurization device (not shown) configured to deliver the fluid 130 from the inlet pipe 150 into the inlet buffer tank 126 of the fluid channel 120*a*, as indicated by an arrow A3, such that the fluid 130 may flow through the connecting structure 129 and in contact with the target 140. Subsequently, the fluid 130 may exit from the housing and enter into the outlet pipe 160*a* through the outlet buffer tank 128, as indicated by an arrow A4. An arrangement direction (e.g., lengthwise direction) of the inlet pipe 150*a* (i.e., a direction of the arrow A3) and an arrangement direction (e.g., lengthwise direction) of the outlet pipe 160*a* (i.e., a direction of the arrow A4) are perpendicular to the lower surface 113 of the housing 110.

In some embodiments, the fluid channel 120*a* further includes an inlet channel and an outlet channel located on the lower surface 113 of the housing 110, in which the inlet buffer tank 126 is connected to the inlet channel and the outlet buffer tank 128 is connected to the outlet channel. In other words, in the direction of the arrow A3, the inlet channel is located between the inlet pipe 150*a* and the inlet buffer tank 126; in the direction of the arrow A4, the outlet channel is located between the outlet pipe 160*a* and the outlet buffer tank 128. The bottom surface 126C of the inlet buffer tank 126 may have an opening to allow the fluid 130 to flow into the inlet channel through the opening. Similarly, the bottom surface 128C of the outlet buffer tank 128 may have an opening to allow the fluid 130 to be discharged into the outlet channel through the opening.

Figure 5:
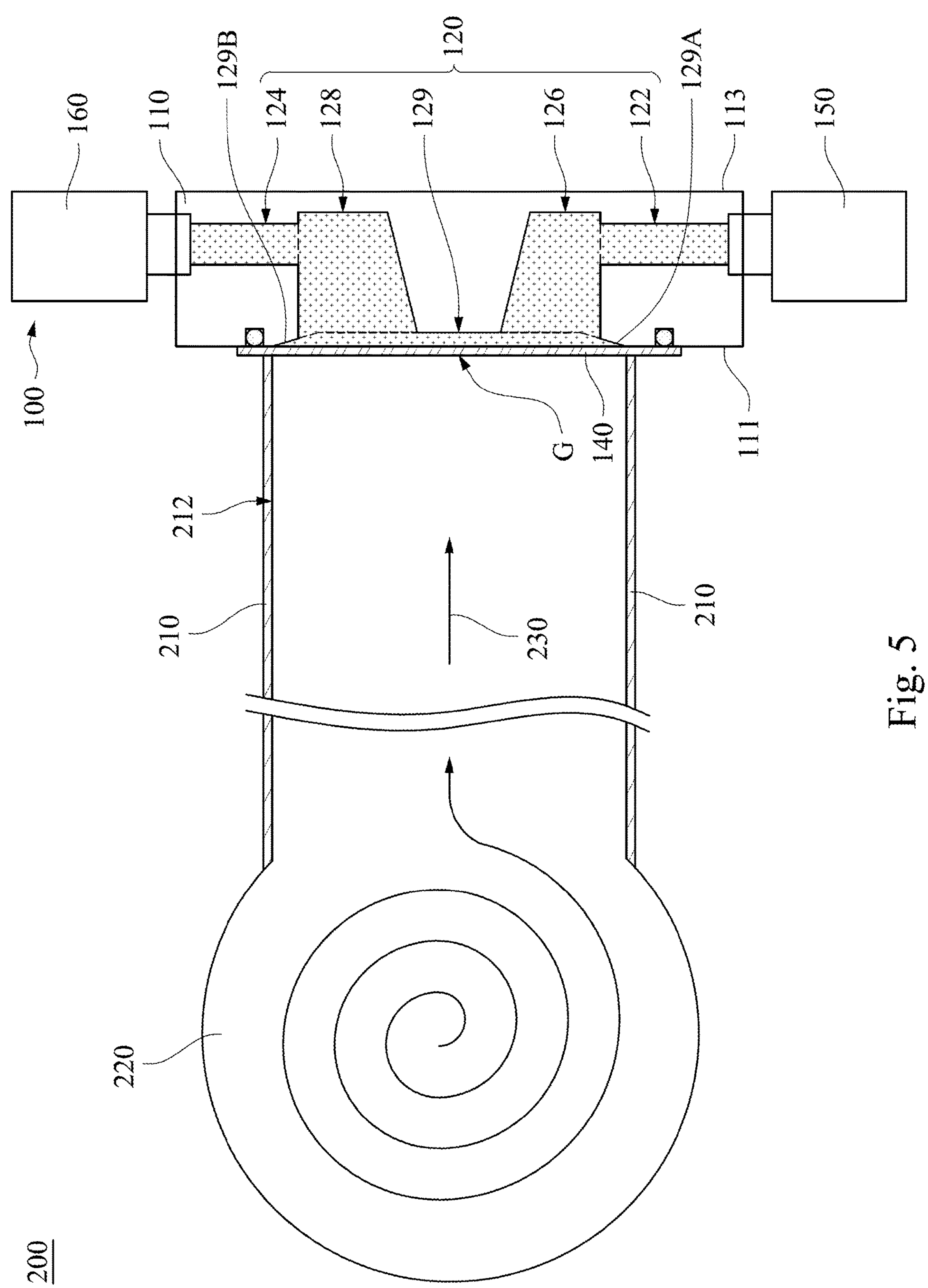
FIG. 5 is a cross-section view of a neutron beam generating device in accordance with an embodiment of the present disclosure.

FIG. 5 is a schematic view of a neutron beam generating device 200 in accordance with an embodiment of the present disclosure. In order to prevent FIG. 5 from being overcomplicated, the proportional relation between each of the layers shown in FIG. 5 is not necessary to be the same as the actual proportion. The structures drawn are used to assist for description only, but are not intended to limit the relation of the relative positions of the layers in the structure. In other embodiments, some of the layers can be omitted while other layers can be added.

Referring to FIG. 5, the neutron beam generating device 200 includes the heat dissipation structure 100, an ion beam tubular body 210, and an accelerator 220. The ion beam tubular body 210 is located above the heat dissipation structure 100 and directed towards the upper surface 111 of the housing 110 of the heat dissipation structure 100, in which a gap G is between the ion beam tubular body 210 and the upper surface 111 of the housing 110. In some embodiments, the gap G between the ion beam tubular body 210 and the housing 110 of the heat dissipation structure 100 is configured to accommodate the target 140. The ion beam tubular body 210 and the upper surface 111 of the housing 110 of the heat dissipation structure 100 are respectively configured to abut two opposite surfaces of the target 140. The target 140 may include beryllium (Be). The ion beam tubular body 210 has a channel 212, and the accelerator 220 is connected to the ion beam tubular body 210, in which the accelerator 220 is configured to emit an ion beam 230 toward the upper surface 111 of the housing 110 of the heat dissipation structure 100 through the channel 212. In other words, the accelerator 220 is configured to emit the ion beam 230 towards the target 140 through the channel 212. In some embodiments, the ion beam 230 generated from the accelerator 220 can pass through the channel 212 and bombard on the target 140, thereby exciting the neutron beam for use in boron neutron capture therapy (BNCT).

In some embodiments, an extension direction of the ion beam tubular body 210 is perpendicular to the upper surface 111 of the housing 110 of the heat dissipation structure 100. In other words, the extension direction of the ion beam tubular body 210 is perpendicular to the two surfaces of the target 140 that abut the ion beam tubular body 210 and the heat dissipation structure 100. In some embodiments, a vertical projection length of the inlet buffer tank 126 on the upper surface 111 of the housing 110 along the first direction D1 is smaller than a vertical projection length of the outlet buffer tank 128 on the upper surface 111 of the housing 110 along the first direction D1. A vertical projection length of the inlet buffer tank 126 on the target 140 along the first direction D1 is smaller than a vertical projection length of the outlet buffer tank 128 on the target 140 along the first direction D1. In some embodiments, the extension direction of the inlet pipe 150 and/or the outlet pipe 160 is perpendicular to an extension direction of the ion beam tubular body 210. In some embodiments, a width of the channel 212 of the ion beam tubular body 210 is substantially aligned with the connecting structure 129. Specifically, the two sides of the channel 212 of the ion beam tubular body 210 are respectively aligned with the first bevel surface 129A and the second bevel surface 129B of the connecting structure 129.

In some embodiments, when the accelerator 220 emits the ion beam 230 towards the target 140 through the channel 212, the density distribution of the emitted ion beam 230 is in the form of Gaussian distribution, such that the heat source distribution of the target 140 bombarded by the emitted ion beam 230 is also in the form of Gaussian distribution. In other words, the target 140 may be referred as a heat source with Gaussian distribution. Since the heat dissipation structure 100 is configured to carry out heat dissipation to this kind of heat source, the heat dissipation structure 100 can prevent the neutron beam generating device 200 from experiencing unexpected damage during operation, such as the burst of the target 140 due to overheat stress. In some embodiments, the accelerator 220 is a cyclotron accelerator.

Figure 6:
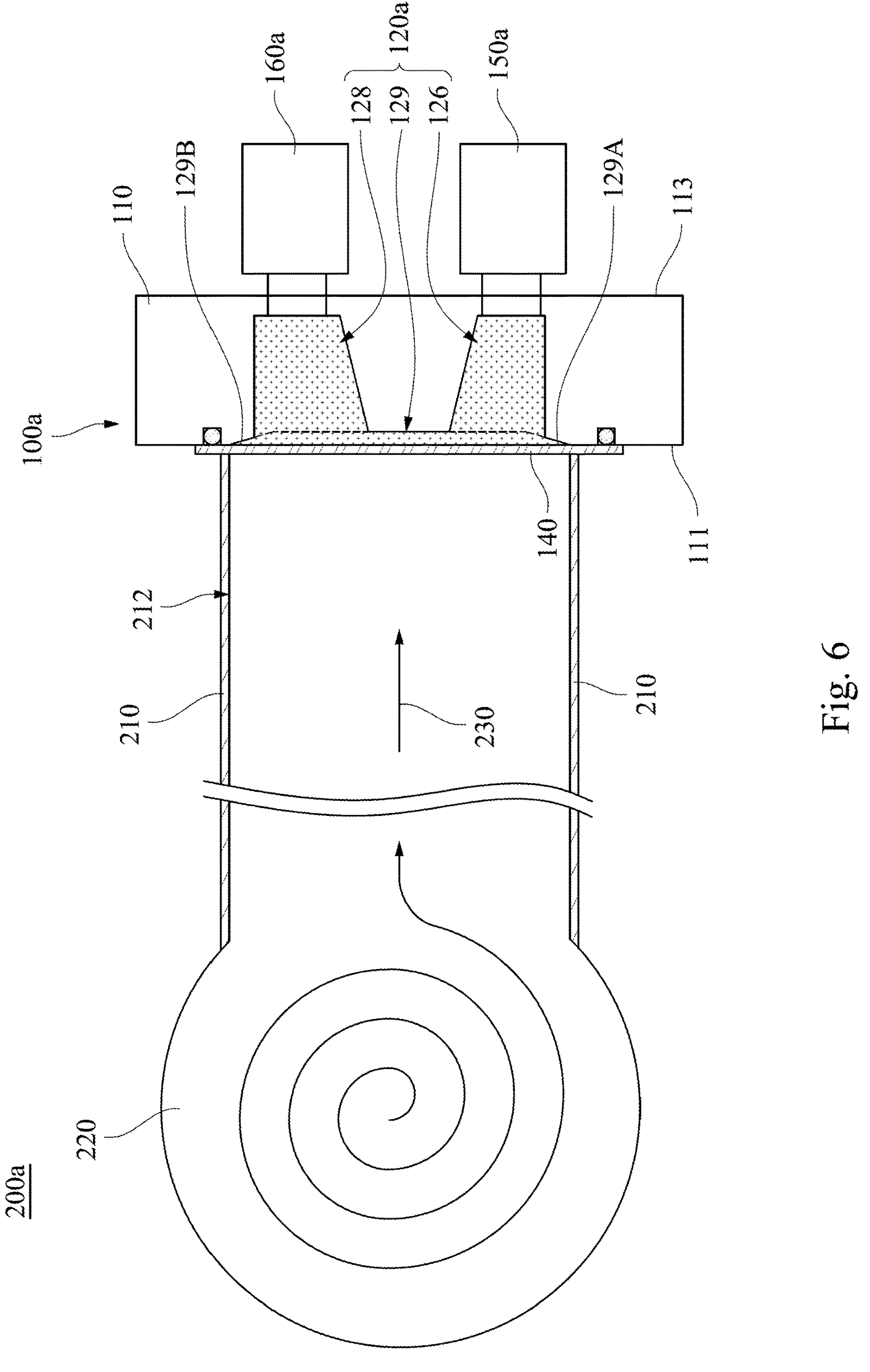
FIG. 6 is a cross-section view of a neutron beam generating device in accordance with another embodiment of the present disclosure.

FIG. 6 is a schematic view of a neutron beam generating device 200*a* in accordance with another embodiment of the present disclosure. The neutron beam generating device 200*a* of FIG. 6 is substantially the same as the neutron beam generating device 200 of FIG. 5, and the difference is the configuration of the heat dissipation structure 100*a*. The inlet pipe 150*a* and outlet pipe 160*a* of the heat dissipation structure 100*a* are located on the lower surface 113 of the housing 110. The extension direction of the inlet pipe 150*a* and/or the outlet pipe 160*a* is parallel to the extension direction of the ion beam tubular body 210. Other descriptions regarding the heat dissipation structure 100*a* may refer to the embodiment of FIG. 4 and will not be repeated here for simplicity.

In summary, since the connecting structure has the first bevel surface and the second bevel surface connecting the upper surface of the housing, the fluid in the fluid channel can be concentrated at the center of the housing (i.e., the center the target corresponding to the center of the housing) and has a faster flowing speed, thereby enhancing the effect of removing the heat from the target. Furthermore, through this mechanism, the heat dissipation structure is suitable (or adaptable) to be applied in the neutron beam generating device.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A heat dissipation structure for a neutron beam generating target, comprising:

a housing having an upper surface, a lower surface opposite to the upper surface, and a fluid channel disposed between the upper surface and the lower surface, wherein the fluid channel is configured to allow a fluid to pass through, and the fluid channel comprises:

an inlet buffer tank having a first inner wall surface and a second inner wall surface opposite the first inner wall surface;

an outlet buffer tank having a first inner wall surface and a second inner wall surface opposite the first inner wall surface, and the second inner wall surface of the outlet buffer tank is closer to the inlet buffer tank than the first inner wall surface of the outlet buffer tank is, wherein the second inner wall surface of the inlet buffer tank is closer to the outlet buffer tank than the first inner wall surface of the inlet buffer tank is;

a connecting structure disposed on the inlet buffer tank and the outlet buffer tank, wherein the connecting structure has a first bevel surface and a second bevel surface directly connected to the upper surface of the housing and in contact with the fluid;

an inlet pipe connected to the inlet buffer tank;

an outlet pipe connected to the outlet buffer tank; and at least one predetermined target position disposed on the upper surface of the housing and disposed above the connecting structure, wherein the at least one predetermined target position is configured to accommodate a target for converting an ion beam into a neutron beam such that the fluid is physically in contact with the target through the connecting structure.

2. The heat dissipation structure of claim 1, wherein the first bevel surface of the connecting structure and the second bevel surface of the connecting structure taper towards the lower surface of the housing.

3. The heat dissipation structure of claim 1, wherein the first bevel surface of the connecting structure is connected to the first inner wall surface of the inlet buffer tank and the second bevel surface of the connecting structure is connected to the first inner wall surface of the outlet buffer tank.

4. The heat dissipation structure of claim 1, wherein the first bevel surface of the connecting structure extends downward from the upper surface of the housing, and the first inner wall surface of the inlet buffer tank extends downward from the first bevel surface of the connecting structure.

5. The heat dissipation structure of claim 1, wherein the second bevel surface of the connecting structure extends downward from the upper surface of the housing, and the first inner wall surface of the outlet buffer tank extends downward from the second bevel surface of the connecting structure.

6. The heat dissipation structure of claim 1, wherein the second inner wall surface of the inlet buffer tank is inclined to the upper surface of the housing, and the second inner wall surface of the outlet buffer tank is inclined to the upper surface of the housing.

7. The heat dissipation structure of claim 1, wherein the second inner wall surface of the inlet buffer tank and the second inner wall surface of the outlet buffer tank taper towards the upper surface of the housing.

8. The heat dissipation structure of claim 1, wherein a slope of the second inner wall surface of the inlet buffer tank is different from a slope of the second inner wall surface of the outlet buffer tank.

9. The heat dissipation structure of claim 8, wherein the slope of the second inner wall surface of the inlet buffer tank is greater than the slope of the second inner wall surface of the outlet buffer tank.

10. The heat dissipation structure of claim 1, wherein when the heat dissipation structure is viewed along a direction perpendicular to the upper surface of the housing, the inlet buffer tank has a first arc-shaped profile and the outlet buffer tank has a second arc-shaped profile different from the first arc-shaped profile.

11. The heat dissipation structure of claim 1, wherein when the heat dissipation structure is viewed along a direction perpendicular to the upper surface of the housing, an arc length of the second inner wall surface of the inlet buffer tank is greater than an arc length of the second inner wall surface of the outlet buffer tank.

12. The heat dissipation structure of claim 1, wherein when the heat dissipation structure is viewed along a direction perpendicular to the upper surface of the housing, a width between the first inner wall surface and the second inner wall surface of the inlet buffer tank is different from a width between the first inner wall surface and the second inner wall surface of the outlet buffer tank.

13. The heat dissipation structure of claim 1, wherein the connecting structure further comprises a bottom surface connected to the second inner wall surface of the inlet buffer tank and the second inner wall surface of the outlet buffer tank.

14. The heat dissipation structure of claim 13, wherein the bottom surface of the connecting structure is inclined to the second inner wall surface of the inlet buffer tank, and the bottom surface of the connecting structure is inclined to the second inner wall surface of the outlet buffer tank.

15. The heat dissipation structure of claim 1, wherein the inlet buffer tank further comprises a bottom surface connected to the second inner wall surface of the inlet buffer tank, and the second inner wall surface of the inlet buffer tank is inclined to the bottom surface of the inlet buffer tank.

16. The heat dissipation structure of claim 1, wherein the outlet buffer tank further comprises a bottom surface connected to the second inner wall surface of the outlet buffer tank, and the second inner wall surface of the outlet buffer tank is inclined to the bottom surface of the outlet buffer tank.

17. The heat dissipation structure of claim 1, wherein a distance between the first inner wall surface and the second inner wall surface of the inlet buffer tank along a direction increases from the lower surface of the housing towards the upper surface of the housing.

18. A neutron beam generating device, comprising:

a heat dissipation structure comprising:

a housing having an upper surface, a lower surface opposite to the upper surface, and a fluid channel disposed between the upper surface and the lower surface, wherein the fluid channel is configured to allow a fluid to pass through, and the fluid channel comprises:

an inlet buffer tank having a first inner wall surface and a second inner wall surface opposite the first inner wall surface;

an outlet buffer tank having a first inner wall surface and a second inner wall surface opposite the first inner wall surface, and the second inner wall surface of the outlet buffer tank is closer to the inlet buffer tank than the first inner wall surface of the outlet buffer tank is, wherein the second inner wall surface of the inlet buffer tank is closer to the outlet buffer tank than the first inner wall surface of the inlet buffer tank is; and a connecting structure disposed on the inlet buffer tank and the outlet buffer tank, wherein the connecting structure has a first bevel surface and a second bevel surface directly connected to the upper surface of the housing and in contact with the fluid;

an ion beam tubular body having a channel, wherein the ion beam tubular body is disposed above the heat dissipation structure and directed toward the upper surface of the housing of the heat dissipation structure, and a gap is between the ion beam tubular body and the upper surface of the housing of the heat dissipation structure; and an accelerator connected to the ion beam tubular body and configured to emit an ion beam toward the upper surface of the housing of the heat dissipation structure through the channel.

19. The neutron beam generating device of claim 18, wherein the ion beam tubular body is perpendicular to the upper surface of the housing of the heat dissipation structure.

20. The neutron beam generating device of claim 18, wherein two sides of the channel of the ion beam tubular body are respectively aligned with the first bevel surface and the second bevel surface of the connecting structure.

* * * * *